(12) United States Patent
Lean et al.

(10) Patent No.: US 7,121,157 B2
(45) Date of Patent: Oct. 17, 2006

(54) HAND-HELD BIO-AGENT COLLECTOR

(75) Inventors: Meng H. Lean, Santa Clara, CA (US); Huangpin Ben Hsieh, Mountain View, CA (US); Armin R. Völkel, Mountain View, CA (US); Peter Kiesel, Palo Alto, CA (US); Noble Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 197 days.

(21) Appl. No.: 10/913,940

(22) Filed: Aug. 6, 2004

(65) Prior Publication Data
US 2006/0027034 A1  Feb. 9, 2006

(51) Int. Cl.
*G01N 1/04* (2006.01)
*G01N 1/22* (2006.01)

(52) U.S. Cl. .................. 73/864.71; 73/863.21
(58) Field of Classification Search ............. 73/863.21, 73/864.41, 864.71, 864.72
See application file for complete search history.

(56) References Cited

U.S. PATENT DOCUMENTS

| | | | |
|---|---|---|---|
| 3,526,219 A * | 9/1970 | Lewis | 600/565 |
| 3,633,405 A | 1/1972 | Noll | |
| 3,684,660 A * | 8/1972 | Kereluk et al. | 435/305.1 |
| 4,558,752 A * | 12/1985 | Freund et al. | 175/207 |
| 5,949,001 A | 9/1999 | Willeke | |
| 6,267,016 B1 | 7/2001 | Call et al. | |
| 6,455,982 B1 | 9/2002 | Hashimoto | |
| 6,532,835 B1 | 3/2003 | Saaski et al. | |
| 6,729,196 B1 | 5/2004 | Moler et al. | |
| 2004/0235155 A1* | 11/2004 | Elander et al. | 435/309.1 |
| 2005/0081655 A1* | 4/2005 | Fine et al. | 73/864.71 |

OTHER PUBLICATIONS

Lean et al., "High Speed MEMS Device for Sample Preparation of Bio-Agent in Water", Proceedings, 2nd Joint Conference on Point Detection for Chemical and Biological Defense, May 2004.*

* cited by examiner

*Primary Examiner*—Charles Garber
(74) *Attorney, Agent, or Firm*—Fay, Sharpe, Fagan, Minnich & McKee, LLP

(57) ABSTRACT

Disclosed is a compact, non-contacting device for collecting samples, and particularly minute quantities of bio-agents or particulates, from a surface. The device vibrates a region of a target surface containing the sample and collects the sample on an electrically charged pin array. The sample can be later released to a detector or other instrumentation for subsequent analysis.

20 Claims, 10 Drawing Sheets

HAND-HELD BIO-AGENT COLLECTOR

BACKGROUND

The present exemplary embodiment relates to the collection of bio-agents and particles. It finds particular application in conjunction with collecting minute sample amounts of bio-agents, and will be described with particular reference thereto. However, it is to be appreciated that the present exemplary embodiment is also amenable to other like applications.

In the biosciences, the detection of miniscule concentrations of bio-molecules, e.g. protein (complexes), viruses, spores, cells, etc., is of high importance. Examples include the detection of low-abundance proteins for understanding cell function or the detection of harmful bio-agents, e.g. toxins, viruses, microbes, spores, parasites, etc., that can pose a risk even at very low concentrations.

The anthrax-by-mail attacks at several US Postal Service (USPS) mail-processing centers in October 2001 resulted in heightened interests in methods to collect and test suspected samples. High flow rate air filtration systems capable of processing hundreds of liters of air per minute were installed in many of these centers. Samples collected on filters are analyzed using portable polymerase chain reaction (PCR) to detect the anthrax (*Bacillus anthracis*) DNA. However, suspicious samples on exposed equipment surfaces are still collected with cotton or polyester swabs and then deposited in test tubes for subsequent PCR analysis. The detection problem is often complicated by low signal to noise measurements as ancillary material, such as dirt, grease or even cotton fibers from the swab used for collection, act to cover up the signature of the anthrax sample; leading to frequent failed assays or intolerable false-positive rates. Accordingly, there is a need for a non-contacting device to collect such samples. And, in the interests of convenience and usability of such a device, it would be beneficial if the device were relatively small and portable.

BRIEF DESCRIPTION

In accordance with one aspect of the present exemplary embodiment, a device is provided for collecting a sample from a target surface. The device comprises a device housing, a vibratory member extending from the housing, and a pin array also extending from the housing. The vibratory member is adapted to transmit vibrations to the target surface. The vibrations overcome particle-to-particle cohesion and particle-to-surface adhesion due to short range van der Waal force, thus allowing the particles to freely migrate along the high field lines toward the pin tips. The vibratory member, which may be a source of physical disturbance as provided by piezo unimorphs or may employ pressure agitation as in ultrasonic devices, defines a distal end for contacting the target surface. The pin array is adapted to receive an electrical voltage and generate an electric field in the vicinity of the target surface when the distal end of the vibratory member contacts the target surface.

In another aspect of the exemplary embodiment, a system is provided for receiving a sample collected from a target surface. The system comprises a device for collecting a sample from a target surface in which the device comprises (i) a device housing, (ii) a vibratory member extending from the housing and adapted to transmit vibrations to the target surface, the vibratory member defining a distal end for contacting the target surface, and (iii) a pin array extending from the housing and adapted to receive an electrical voltage and generate an electric field in the vicinity of the target surface when the distal end of the vibratory member contacts the target surface. The system also comprises a docking station adapted to engage the device and receive the sample collected by the device.

In another aspect of the present exemplary embodiment, a system is provided for collecting a sample from a flowing gas stream. This system comprises a channel for housing and directing the flowing gas stream. The system also comprises a sample collector including a (i) pin array in flow communication with the channel, the pin array having a collection of pins extending transversely within the flow of the gas stream, (ii) an electrical power source for selectively inducing an electric field about the pin array, and (iii) a vibratory component adapted to vibrate the pin array.

In yet another aspect according to the exemplary embodiment, a method is provided for collecting bio-agents from a target surface by use of a device comprising (i) a device housing, (ii) a vibratory member extending from the housing and adapted to transmit vibrations to the target surface, the vibratory member defining a distal end for contacting the target surface, and (iii) a pin array extending from the housing and adapted to receive an electrical voltage and generate an electric field in the vicinity of the target surface when the distal end of the vibratory member contacts the target surface. The method comprises a step of contacting the vibratory member to the target surface. The method also comprises a step of vibrating the target surface by vibrating the vibratory member and transmitting the vibration to the target surface whereby bio-agents are displaced or otherwise released from the target surface. And, the method comprises a step of applying an electric potential to the pin array to thereby emit an electric field from the pin array such that the field extends to the target surface whereby bio-agents are collected on the pin array.

DETAILED DESCRIPTION

The exemplary embodiment described herein relates to a non-contacting, low power consumption, hand-held bio-agent collection device. The term "non-contacting" as used herein refers to a feature of the device in which no contact occurs between the device and sample during collection of the sample. Although once collected, the sample may contact a pin array of the device, no contact occurs during the actual collection of the sample from a target surface. This results in significantly less contaminates being inadvertently collected. The device in certain versions, uses a piezo (PZT) component or circuit to vibrate a contaminated surface in order to fluidize bio-agents or particulates which are subsequently collected using relatively high electric fields emitted about a pin array of the device. The collected samples once collected and retained by the device are then deposited onto a test substrate on a docking station by reversal of the electric field and PZT vibration of the pin array. A detector with associated sample preparation capabilities such as cell lysing and/or denaturing of nucleic acids may be incorporated into alternate implementations of the docking station.

Figure 1A:
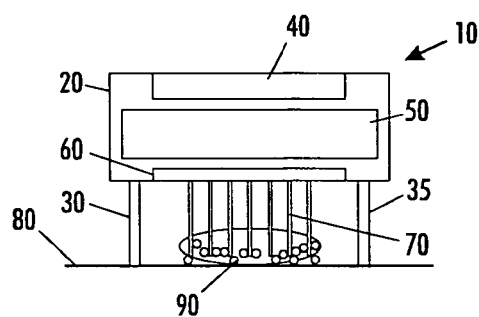
FIG. 1A is a schematic side view of an exemplary embodiment hand-held bio-agent collector.
Figure 1B:
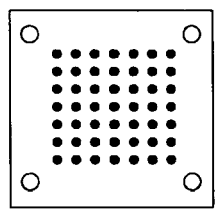
FIG. 1B is a first view of the underside of the bio-agent collector as shown in FIG. 1A biased for conductive surfaces.
Figure 1C:
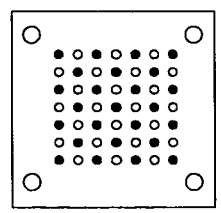
FIG. 1C is a second view of the underside of the bio-agent collector as shown in FIG. 1A for insulative surfaces.
Figure 1D:
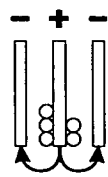
FIG. 1D is a schematic view illustrating a typical collection of pins used in the collector, pin charge, and respective particle arrangement.

An exemplary embodiment device 10 is shown in FIG. 1A. The device 10 includes a module or body 20 having approximate face dimensions of 3 inches by 3 inches, which may be resized for ergonomic and functional considerations. The device 10 also includes a plurality and ideally four legs 30, which serve as spacers between a pin array (described below) and the pick-up, target, or collection surface. Included in the body 20 are a battery or other power source 40, an electronic controller or printed circuit board (PCB) with associated circuitry 50 for control and operation of the device, a piezo (PZT) actuator 60, a pin array 70, and On/Off and mode switches (not shown). FIG. 1B illustrates the underside of the device 10 and shows the arrangement of pins and four legs. To operate, the device 10 is placed onto a surface 80 on its four legs. The pin array 70 does not contact the surface due to the length of the legs. Instead, a nominal gap of from about 100 to about 500 µm is provided to establish a high electric field within the gap between the surface and the distal tips of the pin array. The PZT actuator 60 contacts the surface 80 through one or more of the legs 30 and is selectively actuated to vibrate the surface to free particulates 90 that are attached to surface 80 via van der Waal's force. The amplitude of vibration is small and can be achieved with low (>10V) voltage using a unimorph. The rate of vibration can be any rate effective to displace particles or samples to be collected from the surface. A frequency range between 100 Hz and 10 kHz is contemplated, although the exemplary embodiment includes the use of preferred and optimal frequencies within that range. One of the legs 30 also includes a conductive strip 35 to contact and establish a common electrical ground with the surface 80 if conductive. The fluidized particulates 90 are attracted to the pin tips by Coulomb and dipolar forces because of the very high non-uniform electric fields. For non-conductive surfaces, every other pin in the array may be biased to establish fringing electric fields between adjacent pins, as shown in FIGS. 1C and 1D. In this mode, dipolar forces cause particulates to collect on positively charged pins due to positive dielectrophoresis. In FIG. 1C, the filled dark circles designate positively charged pins, and the open circles designate negatively charged pins.

Figure 2:
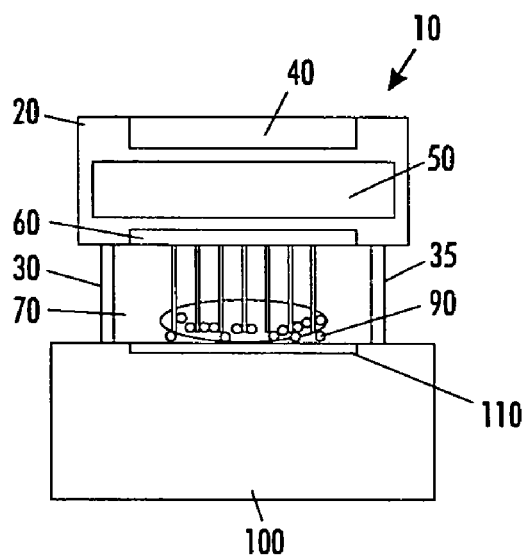
FIG. 2 is a schematic illustration of another exemplary embodiment hand-held bio-agent.

Collected samples may then be deposited onto a sample test surface 110 on a docking station 100 as shown in FIG. 2. This is accomplished by reversing the polarity of the pin array 70 and simultaneously using the PZT actuator 60 to vibrate the pin array to dislodge particulates 90 from the pin tips. It is contemplated that instead of reversing the polarity of the pin array, the electric field can be terminated. For certain applications, termination of the field, particularly coupled with vibration of the pin array, will sufficiently release or dispel collected bio-agents or particles from the pin array. However, either alone may be sufficient to release collected matter. A detector can be integrated onto the docking station 100 to complete the collect/detect capability. For agents such as anthrax, the spores may need to be lysed and nucleic acids denatured prior to DNA hybridization and detection. It is contemplated that these processing capabilities can be incorporated into the docking station 100.

An alternate embodiment for sample collection from non-planar surfaces includes rigidly fixing the pin height with respect to the leg supports. The legs may then be spring mounted to allow for compliance to the pickup surface. The pin array may also be segmented into a group of contiguous sub-arrays with local supports at the four corners to ensure each sub-array conforms to the surface topology.

The exemplary embodiment device can additionally include an inexpensive high voltage amplifier to increase the voltage from that of the battery or power source, e.g. 9V, to ensure sufficiently high electric fields for the operational gap between the pin array and the target surface. For many applications, an electric field of about 1 V/µm is sufficient. However, it will be understood that the exemplary embodiment device can utilize electric fields greater than or lesser than this value. The pin arrays are addressed either collectively or at most in two groups. The exemplary embodiment low power device consumes very low amounts of current, even with a PZT component, so battery life is expected to last for long periods of time, such as for example about 100 hours. The device can easily be built in a modular fashion thereby facilitating rapid replacement of component parts. The pin array may be fabricated inexpensively using connector technology, and is designed to be replaced periodically as it may become contaminated over the course of use. Two methods of fabricating or otherwise providing the pin arrays include, but are not limited to, utilizing 200 µm diameter POGO pins (MEPJ-22BD) on 1 mm pitch; and forming a stressed metal claw array either through sputtering or electroplating at a much finer pitch. The claws would be used only in the open (deployed) position and gap height may be within 10% tolerance in a 100 µm gap, for example. For increased particle collection per unit area, an increased pin density with stressed metal claws would be advantageous. The term "POGO pin" as used herein refers to any suitable spring loaded pin that is typically used in electronic packaging applications. Such pins are commercially available such as from Gold Technologies, Inc. of San Jose, Calif.

The pins can be formed from any electrically conductive material such as, but not limited to, conductive metal alloys such as brass. The configuration and dimensions of the pin array, individual pins, and gap distance (the distance between the distal end of a pin and the target surface) can vary depending upon the specific device characteristics and application. However, exemplary dimensions are as follows. The diameter of a pin of the pin array can range from about 100 µm to about 500 µm. The gap distance can range from about 100 µm to about 500 µm. And the spacing between adjacent pins of the pin array can be from about 200 µm to about 1 mm. The exemplary embodiment includes dimensions greater than or less than these values. The pin array can be in nearly any configuration. Although a rectangular or square array as depicted in the figures is noted, the pin array can be in other arrangements such as a hexagonal close-pack configuration, for example.

One or both of the target surface and the pin array are vibrated as described herein. The vibration can be induced or generated by a PZT component or actuator as known in the art. An example of a commercially available PZT actuator includes the H4 single sheet piezoceramic sheets available from Piezo Systems, Inc. of Cambridge, Mass. Generally, these components operate at up to 50V and 100 KHz. A low amplitude (low voltage) is used but for most applications, a moderate to high frequency excitation (100 Hz to 10 KHz range) is utilized. The optimal operating range could be tailored depending upon the particular system and application.

In certain versions of the device, separate PZT components are used. For instance, a first PZT component, e.g. the H4 piezoceramic sheet, can be used to vibrate the target surface and a second PZT component can be used to vibrate the pin array. The first PZT component is in communication with one or more legs of the device to induce vibration to a region of the surface. Typically, one or more of the legs is larger to thereby incorporate the footprint of the PZT sheet in order to efficiently vibrate the surface. The second PZT component can be integrated adjacent to the body of the device and alongside the pin array to optimize the transfer of vibration from the second component to the pin array. This configuration promotes maximum lateral amplitude in the vibrating pins. Although a PZT component is described for achieving the noted vibration functions, other vibratory components or mechanisms can be utilized.

Figure 3:
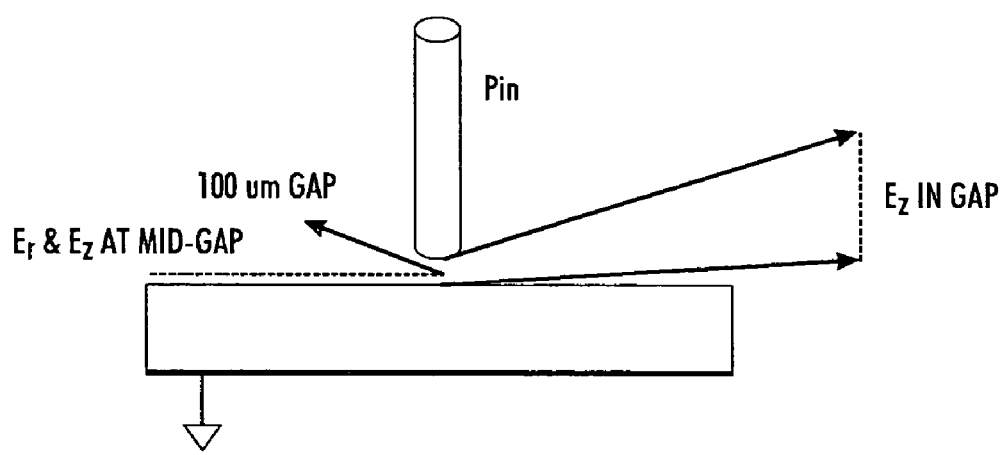
FIG. 3 is a schematic illustration depicting the pin and media to be collected.

A prototype system successfully demonstrated the operability of the exemplary embodiment device using a 9V battery, a pin and emulsion aggregation (EA) toner (EAN12, 1.5% STT 100H+R-812, cyan, 6 µm, 3fC) to act as a substitute for an anthrax agent to be collected. The distal end of the pin was brought within the near vicinity (however without contact) of the toner particles on a surface and the toner was observed to easily collect at the pin tips. Further validation was performed by modeling of the collection pin array, simplified to consideration of a pin-to-plane geometry as shown in FIG. 3.

Figure 4A:
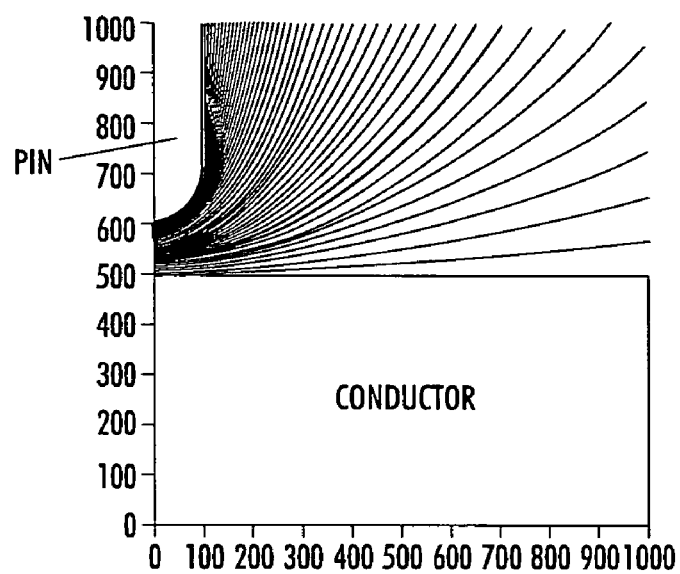
FIG. 4A is a contour plot in air for a pin radius of 100 microns positioned near a conductor.
Figure 4B:
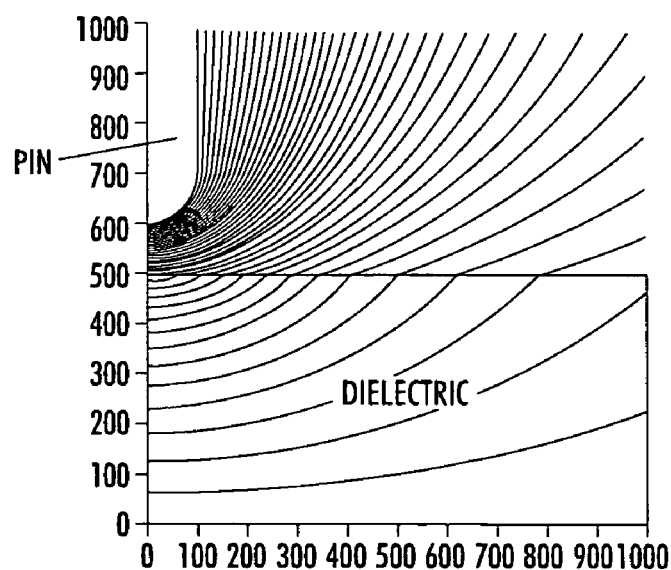
FIG. 4B is a contour plot in air for a pin radius of 100 microns positioned near a dielectric.

FIGS. 4A and 4B illustrate the computed electrical potential contours for the pin-conductor and pin-dielectric configurations, respectively, for a 100 µm radius pin biased at 100V with a 100 µm gap. The surface is assumed to be 500 µm thick, and may represent a coating of paint on postal equipment. The density of contour lines in the vicinity of the pin tip is indicative of the very high E fields.

Figure 5:
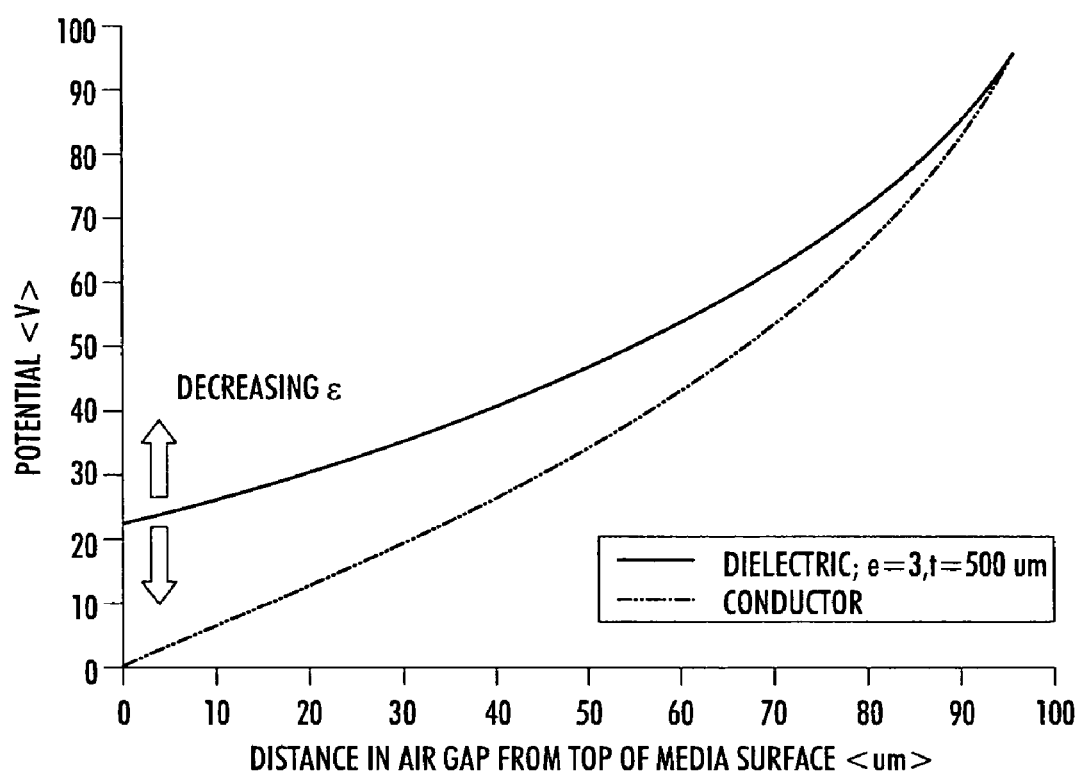
FIG. 5 illustrates axial distribution of electric potential in an air gap for a pin radius of 50 microns.

The voltage drop from the tip of the pin to the collection surface is shown in FIG. 5 for both conducting and dielectric cases. The dielectric constant of the surface material is assumed to be $\epsilon=3$, a number typical of most commercial plastics. For increasing $\epsilon$, the potential curve for the dielectric case (solid) will move downwards toward the conductive case (dashed). As can be seen in FIG. 5, pin-to-conductor results in higher forces, but pin-to-dielectric is comparable especially for high dielectric constant materials.

Figure 6A:
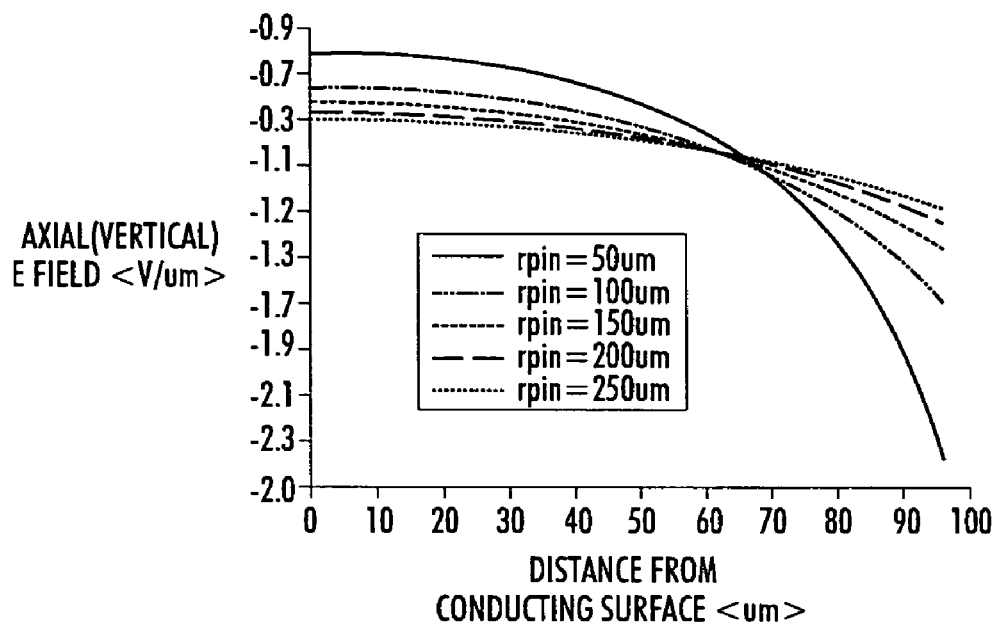
FIG. 6A illustrates the axial electric field in air gaps of various dimensions.
Figure 6B:
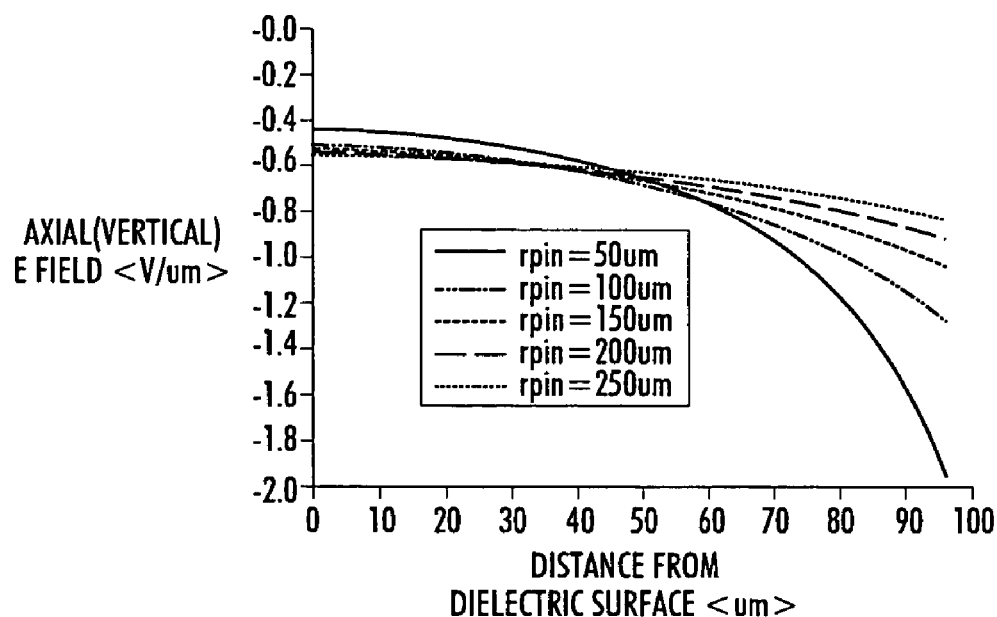
FIG. 6B illustrates the axial electric field in air gaps of various dimensions.

FIG. 6A shows the vertical ($E_z$) component of the E field in the gap between pin and conductor for a range of pin radii: 50, 100, 150, 200, and 250 µm. FIG. 6B illustrates the vertical ($E_z$) component of the E field in the gap between pin and a dielectric for a range of pin radii: 50, 100, 150, 200, and 250 µm. In this and other figures, the designation "rpin" refers to pin radius. The E field is most pronounced for the thinner pin for both configurations. The magnitude of the field is higher in close proximity to the thinner pin but is lower near the collection surface. This data teaches that the advantage of using thinner pins is ensured by also using correspondingly smaller gaps. Significantly higher E fields result from the non-uniform pin-surface configuration as compared to a one-dimensional uniform E field resulting from a parallel plate capacitor, for example.

Figure 7A:
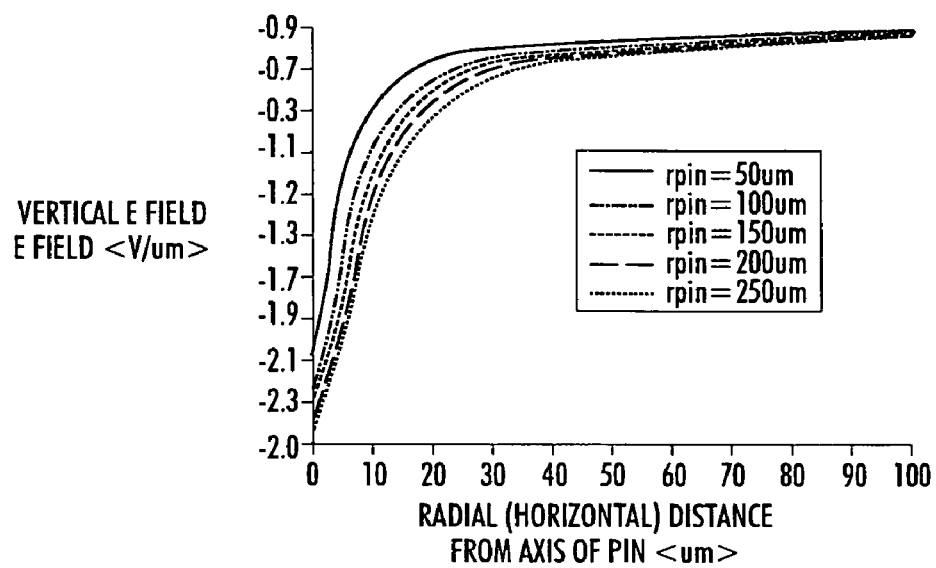
FIG. 7A is a graph illustrating mid-gap distributions of electric field in a radial direction for a range of air gaps.
Figure 7B:
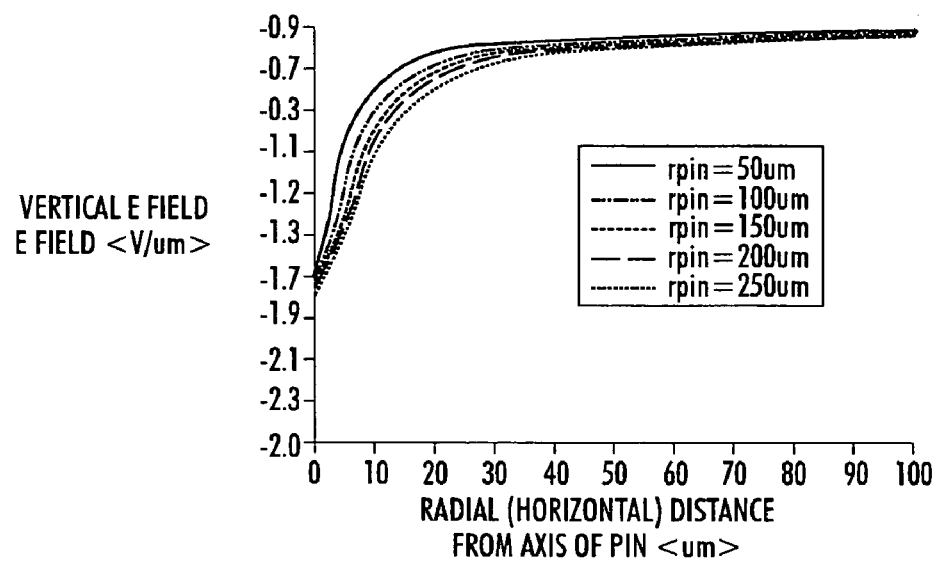
FIG. 7B is a graph illustrating mid-gap distributions of electric field in a radial direction for a range of air gaps.
Figure 8A:
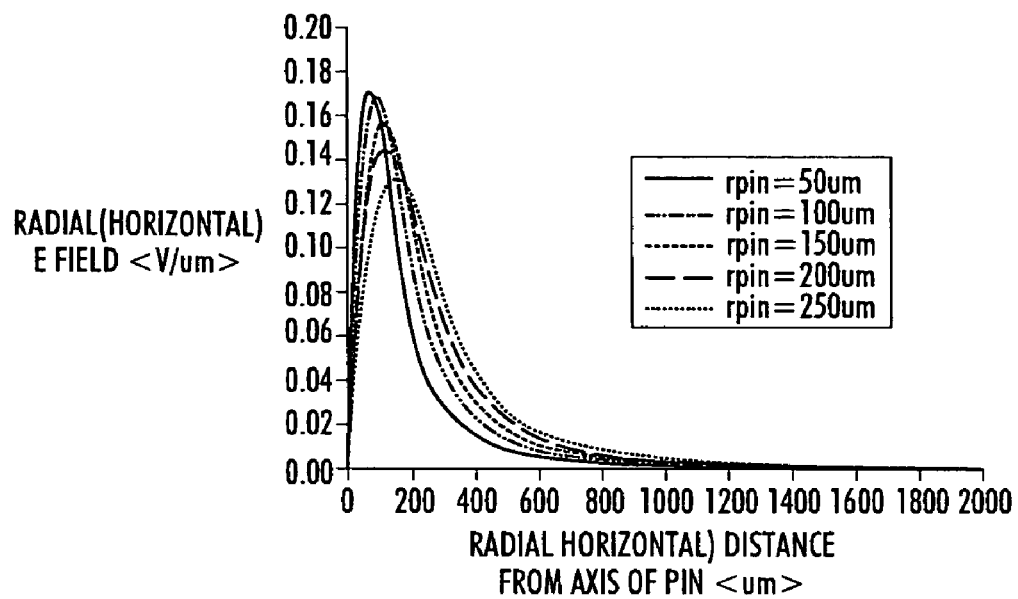
FIG. 8A is a graph of mid-gap distributions of electric field in a radial direction for a range of air gaps.
Figure 8B:
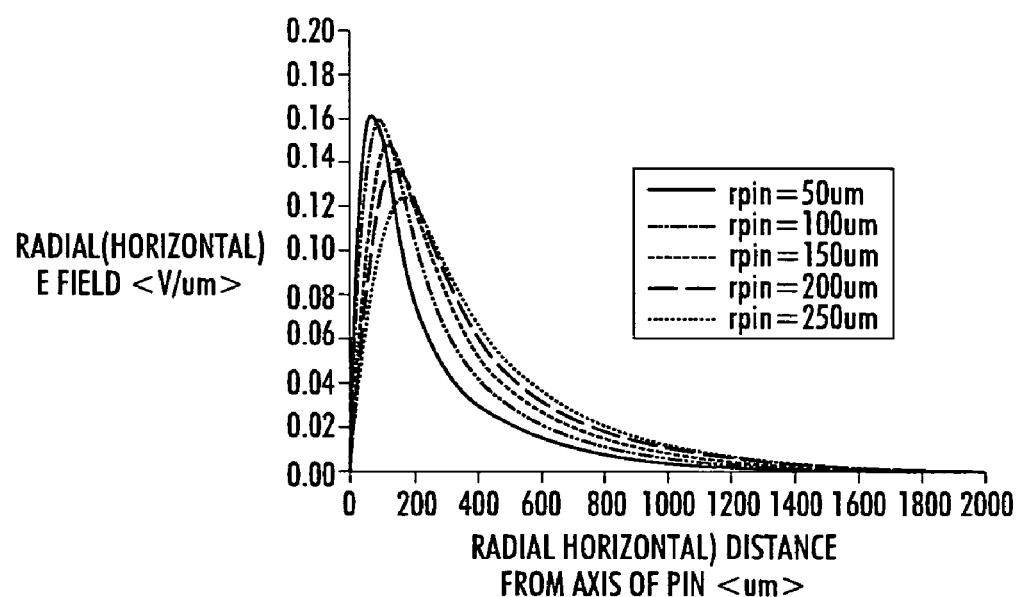
FIG. 8B is a graph of mid-gap distributions of electric field in a radial direction for a range of air gaps.

FIGS. 7A, 7B, 8A and 8B show the vertical ($E_z$) and horizontal ($E_r$) components of the E field in the plane of the surface and at mid-gap. These curves are used to determine the working pitch, or distance between pin centers, which could be a couple of mm. Specifically, FIG. 7A illustrates the vertical E field for a pin to conductor configuration for a variety of mid-gap distributions, ranging from 50, 100, 150, 200, and 250 µm. FIG. 7B illustrates the vertical component of the E field for a pin to dielectric configuration. FIG. 7B illustrates this component for a variety of mid-gap distributions for a similar range of 50, 100, 150, 200, and 250 µm. FIG. 8A illustrates the radial component of the E field for a pin to conductor configuration for a variety of mid-gap distributions such as 50, 100, 150, 200, and 250 µm. Similarly, FIG. 8B illustrates the radial component of the E field for a pin to dielectric configuration for a variety of mid-gap distributions of 50, 100, 150, 200, and 250 µm.

The axial components of forces on the particle are estimated as follows. For a polarizeable particle, the induced dipole moment (Clausius-Mossotti) is:

$$p_{soft}=4\pi a^3 \epsilon_0 (\epsilon-1)/(\epsilon+2)E_z; \epsilon=\epsilon_{particle}/\epsilon_0$$

where a is the particle radius and $\epsilon_{particle}$ is the particle dielectric constant. The permanent dipole moment for a non-uniformly charged particle is:

$$p_{hard}=q_d d; d=2a$$

with $q_d$ and d being the dipole charge and dipole length, respectively. The dipole force is then given by:

$$F_d=(p \cdot \nabla)E=((p_{soft}+P_{hard}) \cdot \nabla)E$$

where the axial component is:

$$F_d=[4\pi a^3 \epsilon_0 (\epsilon-1)/(\epsilon+2)E_z+q_d d]dE_z/dz$$

The Coulomb force is given by:

$$F_c=q_m E_z$$

where $q_m$ is the monopole charge on the particle.

Figure 9:
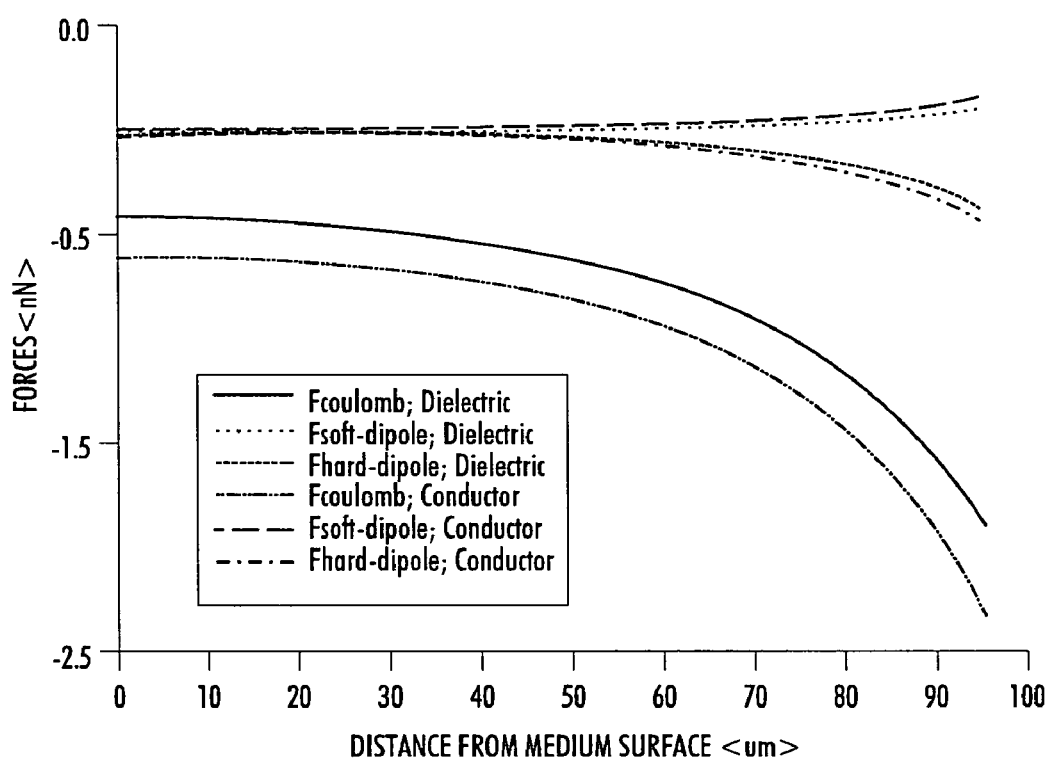
FIG. 9 is a graph illustrating axial force components in an air gap for a 50 micron radius pin.

FIG. 9 illustrates the Coulomb, soft dipole, and hard dipole forces for both conducting and dielectric surfaces. The hard dipole and Coulomb forces are calculated assuming 1 fC of charge, so they need to be scaled to the appropriate magnitudes of monopole and dipole charge, $q_m$ and $q_d$. Clearly, the Coulomb force dominates, although the dipole force can be further enhanced through two methods, such as but not limited to, increasing the E field gradient with finer pin pitch; and/or including an ion source to pre-charge the surface prior to the collection step.

Figure 10A:
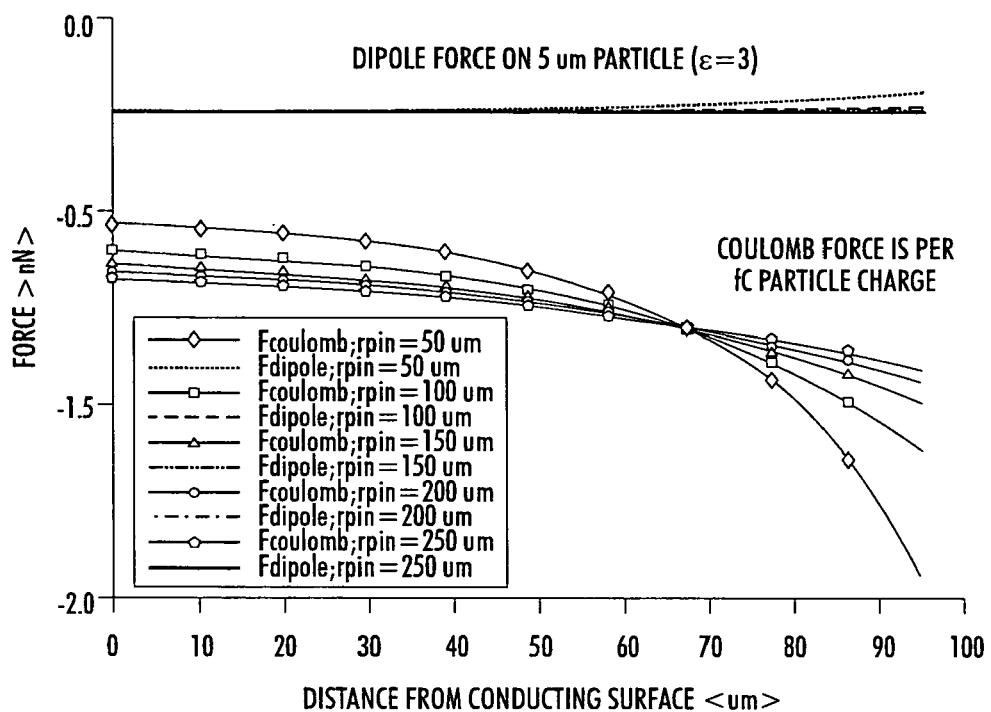
FIG. 10A illustrates axial force components in air gaps for a range of pin radii.
Figure 10B:
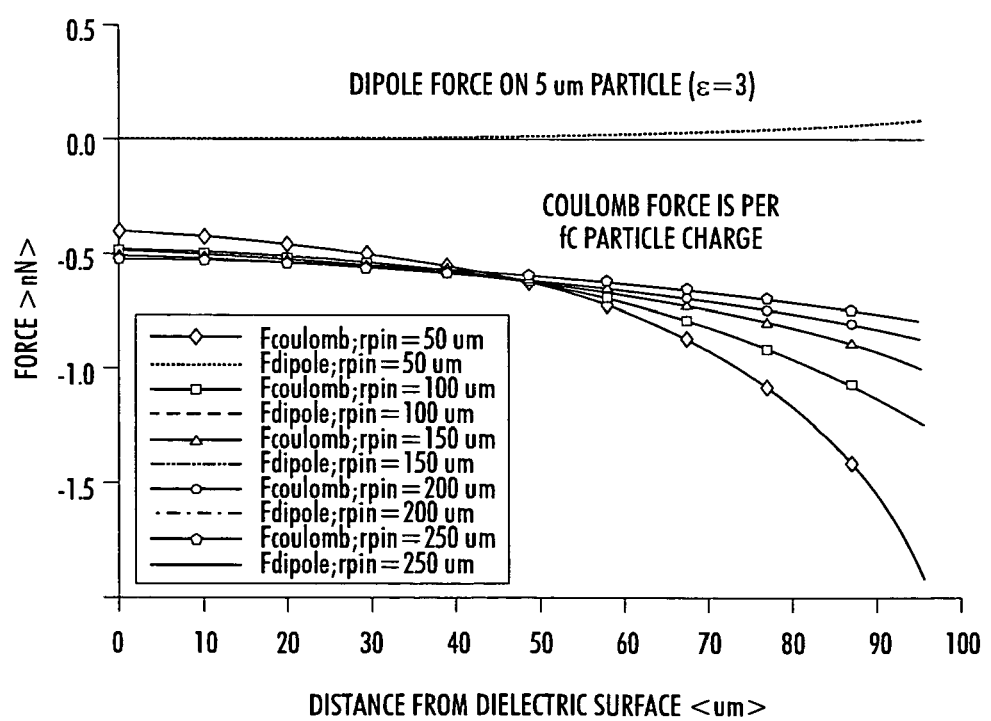
FIG. 10B illustrates axial force components in air gaps for a range of pin radii.

FIGS. 10A and 10B illustrate the Coulomb and soft dipole forces for a range of pin radii: 50, 100, 150, 200, and 250 µm, for a pin to conductor configuration, and for a pin to dielectric configuration. Table 1, set forth below, contains a typical calculation for this EA toner with a density of 1.1853 gm/cm$^3$. The 6 µm diameter toner would have a mass of 1 ng and would require only a force of 10.5 pN to levitate. Therefore, the calculated forces are more than adequate to attract and collect large quantities of particulates.

TABLE 1

Force of Gravity on an Isolated EA Toner Particle

| Parameter | Nominal Value |
|---|---|
| Density <gm/cm$^3$> | 1.1853 |
| r <µm> | 3.0 |
| m <gm> | 1.0725 × 10$^{-9}$ |
| F <N> | 10.51 × 10$^{-12}$ |

A wide array of bio-agents and particles may be selectively collected in accordance with the exemplary embodiment. Generally, bio-agents and particles having a size of from about 10 nm to about 100 µm can be collected using the exemplary embodiment bio-agent collector. Table 2, set forth below, lists several representative bio-agents to which the exemplary embodiment is directed.

TABLE 2

Typical Bio-Agents and Their Dimensions

| | Size | Description |
|---|---|---|
| Bacteria | | |
| Anthrax spore | 1–5 µm | |
| E. coli | 2 µm | |
| Staphylococcus | 2 µm | A category of bacteria that can cause boils, blood poisoning, and other serious infections |
| Virus | | |
| Ebola virus | 200 nm | An extremely contagious filovirus causing an acute, highly fatal hemorrhagic fever and spread through contact with bodily fluids or secretions of infected persons and by airborne particles. |
| Rhino virus | 20 nm | Any of a genus (*Rhinovirus*) of picornaviruses that are related to the enteroviruses and are associated with upper respiratory tract disorders (as the common cold0 |
| Toxin | 1–10 nm | A poisonous substance, especially a protein, that is produced by living cells or organisms and is capable of causing disease when introduced into the body tissues but is often also capable of inducing neutralizing antibodies or antitoxins |
| Oocyte | | |
| mammal | 100 µm | Oocyte: A cell from which an egg or ovum develops by meiosis; a female gametocyte |
| insect | 1000 µm | |
| frog/fish | 1–2 µm | |

TABLE 2-continued

Typical Bio-Agents and Their Dimensions

| | Size | Description |
|---|---|---|
| Toxocara parasite | 75–90 µm | *Toxocara* species are commonly found in wild and domestic animals. The eggs are identified by their thick corrugated shell, size and shape. *Neoascaris vitulorum*, in cattle (egg size 75 µm × 90 µm) |

Another function or application of the exemplary embodiment device is as an aerosol collector or as a collector of entrained particulates which is positioned within a flowing fluidized air stream passing through the pin array. The flow cross-sectional area and flow speed can be adjusted or otherwise controlled for the required flow rate through the device. An ionization unit may be utilized upstream of the airflow to charge airborne particulates so that they can be collected more easily on the pin arrays which can be biased at the opposite polarity.

An example of the ionization unit may be those used in common ionic (electrostatic) air cleaners marketed by many commercial vendors. The basic design consists of a charging cavity with a high voltage pin or wire, a reference voltage grid to create the ionization, and negative charging of the particles entrained in the air stream which flows below the grid. Negatively charged particles are then collected at pin tips biased with a positive voltage.

Figure 11A:
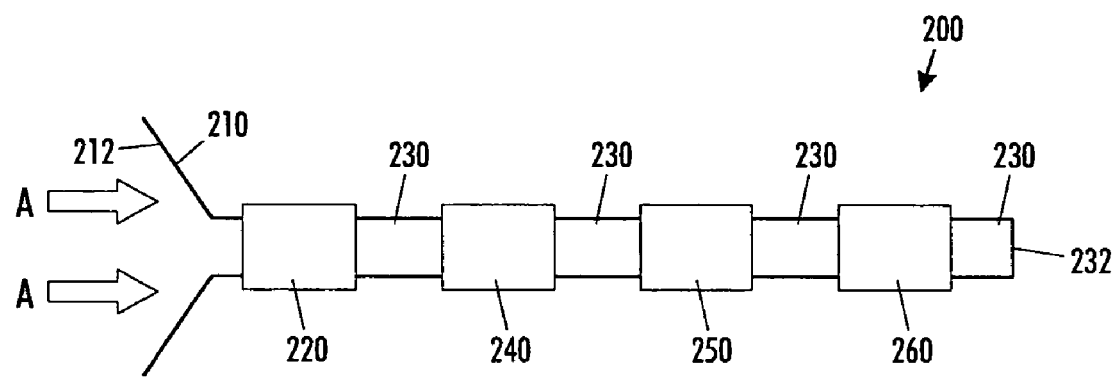
FIG. 11A is a schematic illustration of an exemplary embodiment system.
Figure 11B:
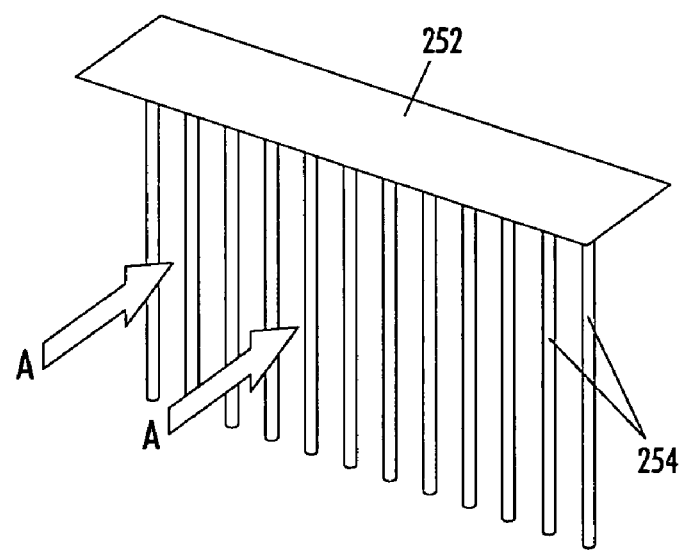
FIG. 11B is a perspective schematic illustration of a pin array used in the exemplary embodiment system of FIG. 11A.

FIG. 11A illustrates an exemplary embodiment system 200 comprising a sample collector for use in a flowing gas stream. It will be understood that the reference to "gas" refers to any fluid or vapor, or mixture thereof. The term specifically includes air. Specifically, referring to FIG. 11A, a stream of flowing gas denoted by arrows A enters an inlet 212 of an air or gas capture enclosure 210. The system 200 also comprises an air handling device 220 such as a fan. Sections of channel or tubing 230 are used to direct flow of the gas or air to be analyzed. The system 200 also includes an optional ionization unit 240 to electrostatically charge particles entrained or otherwise transported in the flowing gas stream. The stream continues down or through the system 200 to a sample collector 250. The sample collector 250 includes a pin array as described in detail herein. Exiting gas departs from system 200 at exit 232. The pin array is in electrical communication with a power source so as to receive a voltage potential across one or more of its pins, to thereby produce an electric field. As will be understood, the electric field causes particles or bio-agents in the gas stream flowing through or past the pin array, to collect along the outer surfaces of the pins. The pin array is also adapted to undergo a vibratory motion to facilitate release of the collected particles from the pin array. Upon release, the particles or bio-agents are collected within the sample collector. FIG. 11B is a detail of an exemplary embodiment pin array of the sample collector 250 shown in FIG. 11A. FIG. 11B illustrates that a plurality of pins 254 of a pin array 252 are oriented, ideally transversely, to the direction of flowing gas. The system 200 may also optionally include one or more post-treatment units 260 such as filters, temperature adjusters, humidity control elements, or detectors.

However, the primary application of the exemplary embodiment device is with a target surface to collect sample particulates or other matter disposed or otherwise retained on the surface. In a related technique, the device can be used in a tiling method. Each hand-held module may cover for example only a three inch by three inch area. Larger area coverage may be realized using "tiling" where the device is lifted and moved over another three inch region in either a vertical, a horizontal, or lateral direction. This procedure can be repeated as necessary to cover much larger collection areas.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A device for collecting a sample from a target surface, the device comprising:
 a device housing;
 a vibratory member extending from the housing and adapted to transmit vibrations to the target surface, the vibratory member defining a distal end for contacting the target surface; and
 a pin array extending from the housing and adapted to receive an electrical voltage and generate an electric field in the vicinity of the target surface when the distal end of the vibratory member contacts the target surface.

2. The device of claim 1 further comprising an electrical power source for providing the electrical voltage to the pin array.

3. The device of claim 1 further comprising a high voltage amplifier chip for providing a higher electrical voltage to the pin array.

4. The device of claim 1 further comprising a second vibratory member adapted to transmit vibrations to the pin array.

5. The device of claim 1 wherein at least one of the vibratory member and the second vibratory member include a PZT component.

6. The device of claim 1 wherein the pin array has a maximum pin length that is less than the length of the vibratory member such that upon placement of the device on the target surface, a gap dimension of from about 100 µm to about 500 µm exists.

7. The device of claim 1 wherein the gap dimension is from about 100 µm to about 200 µm.

8. The device of claim 1 wherein upon operation of the device, the vibrations transmitted from the vibratory member is in the range 100 Hz to 10 KHz.

9. The device of claim 1 wherein upon operation of the device, the electric field generated has a strength of about 1 V/µm.

10. The device of claim 1 wherein the pin array includes a plurality of pins, each having a diameter in the range of from about 100 µm to about 500 µm.

11. The device of claim 1 wherein the pin array includes a plurality of pins, each pin spaced from an adjacent pin by a distance of from about 500 µm to about 1 mm.

12. A system for receiving a sample collected from a target surface, the system comprising:
 a device for collecting a sample from a target surface, the device comprising (i) a device housing, (ii) a vibratory member extending from the housing and adapted to transmit vibrations to the target surface, the vibratory member defining a distal end for contacting the target surface, and (iii) a pin array extending from the housing and adapted to receive an electrical voltage and generate an electric field in the vicinity of the target surface when the distal end of the vibratory member contacts the target surface; and
 a docking station adapted to engage the device and receive the sample collected by the device.

13. The system of claim 12 wherein the docking station includes a sample processing unit that prepares the collected bio-agent samples for subsequent reaction and detection.

14. The system of claim 12 wherein the docking station includes a detector for detecting the presence of a suspected bio-agent.

15. A system for collecting a sample from a flowing gas stream, the system comprising:
 a channel for housing and directing the flowing gas stream; and
 a sample collector including a (i) pin array in flow communication with the channel, the pin array having a plurality of pins extending transversely within the flow of the gas stream, (ii) an electrical power source for selectively inducing an electric field about the pin array; and (iii) a vibratory component adapted to vibrate the pin array to release the sample collected thereon.

16. The system of claim 15 further comprising:
 an ionization source in flow communication with the flowing gas stream and adapted to impart an electrostatic charge to particles or bio-agents in the sample.

17. A method of collecting bio-agents from a target surface by use of a device for collecting a sample from a target surface, the device comprising (i) a device housing, (ii) a vibratory member extending from the housing and adapted to transmit vibrations to the target surface, the vibratory member defining a distal end for contacting the target surface, and (iii) a pin array extending from the housing and adapted to receive an electrical voltage and generate an electric field in the vicinity of the target surface when the distal end of the vibratory member contacts the target surface, the method comprising:
 contacting the vibratory member to the target surface;
 vibrating the target surface by vibrating the vibratory member and transmitting the vibration to the target surface, whereby bio-agents are displaced or otherwise released from the target surface; and
 applying an electric potential to the pin array to thereby emit an electric field from the pin array such that the field extends to the target surface, whereby bio-agents are collected on the pin array.

18. The method of claim 17 further comprising:
 terminating the electric field whereby bio-agents are released from the pin array.

19. The method of claim 17 further comprising:
 reversing the electric potential applied to the pin array to thereby release collected bio-agents from the pin array.

20. The method of claim 16 further comprising:
 vibrating the pin array while either (i) terminating the electric field or (ii) reversing the electric potential applied to the pin array.

* * * * *